(12) United States Patent
Han et al.

(10) Patent No.: US 11,175,289 B2
(45) Date of Patent: Nov. 16, 2021

(54) APPLICATION OF TRPM8 PROTEIN, RELATED PEPTIDE FRAGMENT AND THEIR ANTIBODIES

(71) Applicants: Lei Han, Jiangsu (CN); Xiaohui Zhou, Jiangsu (CN); Yuyan Zhou, Jiangsu (CN); Li Zhou, Jiangsu (CN); Guohua Li, Jiangsu (CN); Yongzhen Li, Jiangsu (CN)

(72) Inventors: Lei Han, Jiangsu (CN); Xiaohui Zhou, Jiangsu (CN); Yuyan Zhou, Jiangsu (CN); Li Zhou, Jiangsu (CN); Guohua Li, Jiangsu (CN); Yongzhen Li, Jiangsu (CN)

(*) Notice: Subject to any disclaimer, the term of this patent is extended or adjusted under 35 U.S.C. 154(b) by 579 days.

(21) Appl. No.: 15/352,607

(22) Filed: Nov. 16, 2016

(65) Prior Publication Data

US 2017/0219603 A1    Aug. 3, 2017

(51) Int. Cl.
| | | |
|---|---|---|
| *C07K 14/705* | (2006.01) | |
| *G01N 33/564* | (2006.01) | |
| *C07K 16/28* | (2006.01) | |

(52) U.S. Cl.
CPC ......... *G01N 33/564* (2013.01); *C07K 14/705* (2013.01); *C07K 16/28* (2013.01); *G01N 2800/342* (2013.01)

(58) Field of Classification Search
CPC .. C07K 14/705; C07K 16/28; G01N 33/6872; G01N 33/564
See application file for complete search history.

(56) References Cited

U.S. PATENT DOCUMENTS

2007/0101444 A1* 5/2007 Brice ................ A01K 67/0276
                                                                800/3

FOREIGN PATENT DOCUMENTS

| CN | 105315357 A | * | 10/2016 | ......... C07K 14/4713 |
| WO | WO-2015123331 A1 | * | 8/2015 | ........... C07K 14/705 |

OTHER PUBLICATIONS

Morgan et al. "Human TRPM8 and TRPA1 pain channels, including a gene variant with increased sensitivity to agonists (TRPA1 R797T), exhibit differential regulation by SRC-tyrosine kinase inhibitor" Biosci. Rep. (2014) 34(4), art:e00131.doi 10.1042/BSR20140061.*
Tsurada et al. "Coiled Coils Direct Assembly of a Cold-Activated TRP Channel" Neuron 51, 201-212, Jul. 20, 2006, DOI 10.1016/j.neuron.2006.06.023.*
Miller et al. "Antibodies to the Extracellular Pore Loop of TRPM8 Act as Antagonists of Channel Activation" PLoS One 9(9): e107151. doi:10.1371/journal.pone.0107151 (Year: 2014).*
Zhang et al. "An Immunogenic Peptide, T2 Induces Interstitial Cystitis/Painful Bladder Syndrome: an Autoimmune Mouse Model for Interstitial Cystitis/Painful Bladder Syndrome" Inflammation Dec. 2017;40(6):2033-2041. doi: 10.1007/S10753-017-0643-0 (Year: 2017).*

* cited by examiner

*Primary Examiner* — Christine Foster
(74) *Attorney, Agent, or Firm* — Honigman LLP; Thomas A. Wootton, Esq.; Jonathan P. O'Brien

(57) ABSTRACT

A TRPM8 related peptide fragment, comprising amino acid sequence as shown in SEQ ID No: 1-18 is provided. Furthermore, application of TRPM8 protein, TRPM8 related peptide fragment and their antibodies in preparing diagnostic reagent for chronic prostatitis/chronic pelvic pain syndromes (CP/CPPS) is provided. By detecting level of TRPM8 protein molecule, TRPM8 related peptide fragment and their antibodies, the chronic prostatitis/chronic pelvic pain syndromes (CP/CPPS) is effectively diagnosed, and the present invention is capable of effectively making a distinction between CP/CPPS and other diseases of prostate. In addition, by intravenously or subcutaneously injecting 1~30000 IU TRPM8 protein or TRPM8 related polypeptide fragments with or without combining nanoparticles for desensitization therapy, or monoclonal or polyclonal antibodies of the TRPM8 protein or polypeptide fragments, the present invention is capable of curing or significantly relieve clinical symptoms of the chronic prostatitis/chronic pelvic pain syndromes (CP/CPPS) and having an therapeutic effect.

5 Claims, 5 Drawing Sheets
Specification includes a Sequence Listing.

APPLICATION OF TRPM8 PROTEIN, RELATED PEPTIDE FRAGMENT AND THEIR ANTIBODIES

BACKGROUND OF THE PRESENT INVENTION

Field of Invention

The present invention relates to the field of immune diagnostic reagent and pharmacotherapy, and more particularly to an application of TRPM8 protein, related peptide fragment and their antibodies in diagnosis of chronic prostatitis/chronic pelvic pain syndromes (CP/CPPS); and an application of the TRPM8 protein, the related peptide fragment and corresponding monoclonal antibody and polyclonal antibody in treating chronic prostatitis/chronic pelvic pain syndromes (CP/CPPS).

Description of Related Arts

Prostatitis is a common disease in the adult male. In China, the incidence of prostatitis among the population of men is 8.4%. Prostatitis patients account for 8~25% of patients in urology surgery. Data shows that about 50% of male are affected by prostatitis in some stage of lifetime.

Prostatitis is currently classified into four types. A III type prostatitis includes a IIIa subtype chronic prostatitis and a IIIb subtype chronic prostatitis/chronic pelvic pain syndromes, which is equivalent to the chronic nonbacterial prostatitis and prostatodynia in a traditional classification method. The III type prostatitis is the most common types of prostatitis and accounts for about over 90% of the chronic prostatitis. The major performances of the chronic prostatitis/chronic pelvic pain syndromes is long-term and repeated pain or discomfort on the pelvic region which lasts for over 3 weeks and varying degrees of urinary symptom and sexual dysfunction, which has a great impact on the life quality of the patients. Meanwhile, the large group of patients and the high medical cost is a great financial burden to the public health.

Since the pathogeny, pathogenesis and pathophysiological change of chronic prostatitis/chronic pelvic pain syndromes (CP/CPPS) is still not clear, and there is still not a clear standard for definite diagnosis of prostatitis, judgment of illness severity, selection of treatment methods and evaluation of therapeutic efficiency and etc., the vast majority of clinicians have difficulty in clinical diagnosis and treatment of prostatitis process.

In 2001, Tsavaler etc. utilizing human prostate-specific complementary DNA library approach identified a novel gene. This gene encodes a protein molecular with weight of about 130 ku and the protein has highly homologous with TRP channel proteins, and thus was named TRPM8. Human gene encoding TRPM8 is located on the site chromosome 2q37.1, with a total length of 102.12 kb, consisting of 25 exons. The mRNA encoding may be translated as protein containing 1104 amino acids. Analysis of published Genome sequence shows that TRPM8 was expressed in all vertebrates studied thermostat. Julius et al. found that TRPM8 is a cold activated temperature sensation TRP channels. Tsavaler etc. found that TRPM8 is also expressed in some primary tumors such as breast, colon cancer, lung and skin sources. Subsequent studies found that TRPM8, mRNA or protein also exists in sensory neurons of dorsal root ganglia and trigeminal, vagus mesenteric ganglion, gastric, vascular smooth muscle, liver, bladder epithelium and male reproductive system.

SUMMARY OF THE PRESENT INVENTION

The present invention discloses an application of TRPM8 protein, related peptide fragment and their antibodies in manufacturing diagnostic reagent and therapeutic drug of chronic prostatitis/chronic pelvic pain syndromes (CP/CPPS). Utilizing a technical principle of monoclonal antibody, the present invention developed TRPM8 antibody ELISA diagnostic kit or fluorescence immunoassay chromatography/homogeneous immunofluorescence diagnostic reagents. The present invention is capable of quickly and specifically whether a patient has chronic prostatitis/chronic pelvic pain syndromes, CP/CPPS and assess development or therapeutic effect of the sickness, in such a manner that patient of chronic prostatitis/chronic pelvic pain syndromes, CP/CPPS is treated in time, so as to improve quality of life of patients Otherwise, the patient can be treated by applying TRPM8, TRPM8 related peptide fragment (desensitization therapy), or anti-TRPM8 protein, antibody of related peptide fragment of the patient of chronic prostatitis/chronic pelvic pain syndromes, CP/CPPS.

Specific technical solution of the present invention is as follows. Hereafter a human-resourced TRPM8 protein is taken as an example.

A TRPM8 related peptide fragment, which is characterized in comprising amino acid sequence as shown in SEQ ID No: 1-18.

The TRPM8 related peptide fragments of the present invention is selected from peptide fragments with different length in the entire amino acid sequence of TRPM8 protein. Taking human-derived TRPM8 as an example, e.g.:

1025-1104 sections of the TRPM8 protein fragment comprise an amino acid sequence selected from the group consisting of:

TRPM8-1: KINTKANDTSEEMRHRFRQLDTKLND (SEQ ID: No 1), wherein the sequences of TRPM8-1 are capable of combining with Biotin, i.e., Vitamin H, so as to form a stable structure; and TRPM8-2: FKNEDNETLAWEGVMKENYL (SEQ ID: No 2), wherein the sequences of TRPM8-2 are capable of combining with Biotin, i.e., Vitamin H, so as to form a stable structure; or 916-953 sections of the TRPM8 protein fragment comprise an amino acid sequence of TRPM8-3: DGTTYD-FAHCTFTGNESKPL (SEQ ID: No 3), wherein the sequences of TRPM8-3 are capable of combining with Biotin, i.e., Vitamin H, so as to form a stable structure; or 1-692 sections of the TRPM8 protein fragment comprise an amino acid sequence selected from the group consisting of:

TRPM8-4: VSRNLGPKIIMLQ (SEQ ID: No 4), wherein the sequences of TRPM8-4 are capable of combining with Biotin, i.e., Vitamin H, so as to form a stable structure;

TRPM8-5: DEVRQWYVNGVNYFTD (SEQ ID: No 5), wherein the sequences of TRPM8-5 are capable of combining with Biotin, i.e., Vitamin H, so as to form a stable structure;

TRPM8-6: LTVIKMEEAGDEIVSNA (SEQ ID: No 6), wherein the sequences of TRPM8-6 are capable of combining with Biotin, i.e., Vitamin H, so as to form a stable structure;

TRPM8-7: CKEKN MESSV CCFKN EDNET;

TRPM8-8: CSEEM RHRFR QLDTK LNDLKG;

TRPM8-9: CFTGNE SKPLCV ELDEII NLPRFPE;

TRPM8-10: NRRND TLDST RTLYSS;

TRPM8-11: VEVED ALTSS AVKEK LVRFC;
and

TRPM8-12: CEMDI ELHDV SPITRH.

1025-1104 sections of the TRPM8 protein fragment comprise an amino acid sequence selected from the group consisting of:

```
                                    (SEQ ID: No 13)
TRPM8-13: KEKNMESSVCCFKNEDNET,
and
                                    (SEQ ID: No 14)
TRPM8-14: SEEMRHRFRQLDTKLNDLKG;
```

916-953 sections of the TRPM8 protein fragment comprise an amino acid sequence of TRPM8-15: FTGNESKPLCVELDEHNLPRFPE (SEQ ID: No 15);

1-692 sections of the TRPM8 protein fragment comprise an amino acid sequence selected from the group consisting of:

```
                                    (SEQ ID: No 16)
TRPM8-16: NRRNDTLDSTRTLYSSASRSTDLSYS;

(SEQ ID: No 17)
TRPM8-17: VEVEDALTSSAVKEKLVRF;
and
                                    (SEQ ID: No 18)
TRPM8-18: EMDIELHDVSPITRH.
```

The present invention further discloses an application of TRPM8 protein, TRPM8 related peptide fragment and their antibodies in preparing diagnostic reagent for chronic prostatitis/chronic pelvic pain syndromes (CP/CPPS).

The TRPM8 protein of the present invention may be selected from any animal origin, preferably mammal origin, more preferably human origin. Taking human or murine origin as an example, and information is as shown in Table. 1.

TABLE 1

| Species | Human | Murine |
| --- | --- | --- |
| Entrez | 79054 | 171382 |
| Ensembl | ENSG00000144481 | ENSMUSG00000036251 |
| UniProt | Q7Z2W7 | Q148W9 |
| mRNA sequence | NM_024080 | NM_134252 |
| Protein sequence | NP_076985 | NP_599013 |
| Gene location | Chr 2: 234.49-234.59 Mb | Chr 1: 90.15-90.22 Mb |

In the application of the present invention, the diagnostic reagent may be but is not limited to immunodiagnostics, biochemical diagnostic reagents, fluorescent reagents or immunological diagnostic chromatography homogeneous immunofluorescence diagnostic reagents.

According to a preferred embodiment of the present invention, TRPM8 protein and TRPM8 related peptide fragment is utilized for detecting antibodies of TRPM8 protein and TRPM8 related peptide fragment from including, but not limited to, serum, plasma, liquor prostaticus and other body fluids of organism or human beings, or utilizing monoclonal antibody or polyclonal antibody of synthetic TRPM8 protein or polypeptide associated TRPM8 fragments prepared by any species or animals to detect level of TRPM8 protein or TRPM8 related peptide fragments in humor of comprising but not limited to serum, plasma or liquor prostaticus.

The above-mentioned immunological method comprises: (but not limited to)

Enzyme immunoassay, including heterogeneous enzyme immunoassay, homogeneous enzyme immunoassay;

Chemiluminescent immunoassay detecting by fluorescent immunoassay method, electrochemiluminescence immunoassay method or chemiluminescence immunoassay determination method and comprising enzymatic chemiluminescence and non-enzymatic chemiluminescence;

Radioimmunoassay analysis comprising: radioimmunoassay, immunoradiometric assay, or measurement analysis (IRMA) methods;

Immune turbidity analysis comprising: immunization nephelometry method and immune nephelometry method;

Time-resolved fluorescence immunoassay and etc.

In the ELISA method, for example, specific method is as follows. Purified human TRPM8 protein or TRPM8 related polypeptide fragments is diluted by coating with buffer solution and coated in a micro-pore of an ELISA plate to form solid-phase antigen, adding confining liquid; respectively diluting a standard and a serum sample to be detected and then adding the standard and the serum sample to be detected to an antigen determination hole, wherein each of the holes is added with enzyme marking reagent of anti-human IgG antibody marked by horseradish peroxidase, so as to form a TRPM8-antibody-enzyme marked and secondary anti-composition, after washing thoroughly in washing liquid, adding enzyme chromogenic substrate solution for coloration, an acidic stopping solution is added when the enzyme substrate solution reaches reaction time, wherein the enzyme substrate solution discolors after thoroughly washed by washing liquid and adding with horseradish peroxidase and then is converted to a final color, wherein color shades are utilized to detect level of TRPM8 protein antibody of samples.

Alternatively, purified anti-human IgG antibody is diluted by buffer coating and then coated within micro-pore of an ELISA Plate made by coating the solid phase antibody in the version of the enzyme within the pores, blocking solution was added; the serum sample to be tested with a standard sample diluent is added after each antibody assay wells per well containing horseradish peroxidase labeled human TRPM8 protein TRPM8 antibody or antibody fragment associated polypeptide enzyme reagent to form TRPM8 antibody HRP secondary antibody complex, after thoroughly washing the washing liquid enzyme chromogenic substrate solution by adding acidic solution after the termination of the enzyme substrate solution to the reaction time, the enzyme substrate solution discoloration under horseradish peroxidase catalysis and under the action of acid converted into the final color, and using color shades to detect levels of TRPM8 protein sample.

In a homogeneous immunological method, for example, specific methods are: respectively pasting an NC film, an absorbent pad, conjugate pad sprayed with fluorescent-labeled antibody and glass fiber which is infiltrated in developing solvent and then dried, in such a manner that an immuno-chromatographic strip is assembled. TRPM8 protein or TRPM8 related polypeptide fragments are evenly sprayed on the NC film by a non-contact micro-sprinkler a three-dimensional spraying platform to form 2 lines in parallel including a non-contact micro-sprinkler T line for coating antigen and a C line of goat anti human/rat IgG T line;

putting the immuno-chromatographic strip in an incubator to keep 37° C. for 1 h and taking out; cutting the immuno-chromatographic strip into a plurality of paper slips with a size at a range of 4 mm±2 mm, and sending the plurality of paper slips to an aluminum foil bag with desiccant for a sealed preservation;

dropping liquid to be detected on an appropriate position of the test trip, performing chromatography, shooting and detecting under a characteristic excitation wave length of 320 nm and an emission wavelength of 620 nm;

performing sensitivity, specificity and simulation of positive samples according to the method mentioned above;

wherein when the samples to be detected is siphoned from bottom to top along the paper slip by capillary action, according to chromatographic theory, the samples to be detected is moved from a detecting end of the paper slip to the other end of the paper slip, wherein the samples to be detected respectively passes through the conjugate pad, the NC film, the T line and the C line to reach the absorbent pad.

After the chromatography, if the C line is not colored, the paper strip is considered invalid; if the C line develops color, the paper strip is considered valid; if the C line develops colors but the T line is not colored, the test result is positive; if both the T line and the C line develop color, the test result is negative.

Taking an enzyme immunoassay method by fluorometric assay as an example, a specific method comprises steps of:

culturing 0.1 ml standard liquid or serum to be mixed with 0.01 ml antibodies or blank antibody reagents at a temperature of 30° C. for 30 min; adding 0.04 ml enzymic reagents mixture for culturing at 15° C. for 30 min; and adding 0.45 ml substrate for culturing at 30° C. for 1 h, adding 0.05 ml sodium alkyl sulfate with a mass concentration of 13 g/L to terminate the reaction, and testing NADPH formed by fluorescence method.

The present invention discloses relationships between chronic prostatitis or chronic pelvic pain syndrome and contents of TRPM8 of body fluid from human body comprising serum, plasma and liquor prostaticus and their antibodies. The chronic prostatitis and chronic pelvic pain syndrome is an autoimmune disease caused by decreasing of tolerance of in-vivo TRPM8 protein and attacking of cells capable of expressing the TRPM8 protein by autoimmune system. Thus, testing levels of TRPM8 protein or its antibodies in body fluids comprising serum, plasma and liquor prostaticus is capable of determining clinical diagnosis of chronic prostatitis/chronic pelvic pain syndromes (CP/CPPS) and evaluating progression and therapeutic effect of the disease.

According to the incidence status of chronic prostatitis/chronic pelvic pain syndromes (CP/CPPS) in the patients and after statistical analysis of the patients, the relationships between morbidity of the chronic prostatitis/chronic pelvic pain syndromes (CP/CPPS) and expression or detection quantity of TRPM8 protein or its antibodies are as shown in Table. 2.

TABLE 2

| Incidence condition | Blood expression or detection amount of TRPM8 protein (ng/ml) | Blood expression or detection amount of TRPM8 antibody (ng/ml) |
| --- | --- | --- |
| Chronic prostatitis/chronic pelvic pain syndromes, CP/CPPS severe | ≥50; <200 | ≥250; <500 |
| Chronic prostatitis/chronic pelvic pain syndromes, CP/CPPS moderate | ≥30; <50 | ≥15; <25 |
| Chronic prostatitis/chronic pelvic pain syndromes, CP/CPPS mild | ≥10; <30 | ≥5; <15 |
| Normal individuals | <10 | <5 |
| Bacterial prostatitis | <10 | <5 |
| Prostate cancer | ≥500 | ≥2000 |

The monoclonal antibodies of the TRPM8 protein and its related peptide fragments can be prepared by the conventional process in the field.

The present invention also discloses a method for chronic prostatitis or chronic pelvic pain syndrome ELISA diagnostic kit, wherein the kit comprises:

(1) TRPM8 protein which is coated or solid carrier of TRPM8-related polypeptide fragment which is free of absorbent and an enzyme-marked IgG antibody which is a conjugate, preferably anti-human IgG antibody, or a solid carrier coated by IgG antibody which is free of absorbent, preferably anti-human IgG antibody, and an enzyme-marked TRPM8 protein antibody or TRPM8-related polypeptide fragment or a combination thereof, wherein amino acid sequences of the TRPM8 protein related peptide fragments are as shown in SEQ ID No: 1-18 below;

(2) Substrate for the enzyme;

(3) Negative control and positive control in a qualitative test, and reference standards and control serum in a quantitative test;

(4) Diluent of the combination and samples;

(5) Washing solution, in a plate ELISA, frequently utilized diluent is phosphate buffered saline containing 0.05% Tween20;

(6) Enzyme reaction-terminated liquid, commonly used HRP terminated solution is sulfuric acid, its concentration and dosage is according to additive amount and the final volume of the colorimetric solution, generally adopting 2 mol/L in a plate ELISA.

The present invention also discloses a test strip for diagnosis of chronic prostatitis/chronic pelvic pain syndromes (CP/CPPS), which is characterized in that the strip has a stationary phase of a fiber chromatography material in a shape of a trip comprising a test line T and a control line C which are fixed thereon. The test line T is coated with TRPM8 protein in a shape of a strip or a belt or TRPM8 related peptide fragments, and the C test line is coated with IgG antibody in a shape of a strip or a belt. The TRPM8 related antibody of the test sample has a specific immune response on the test line T, and other free substances of the samples to be tested has immune responses on the control line C.

The present invention also discloses a test strip for diagnosis of chronic prostatitis/chronic pelvic pain syndromes (CP/CPPS), which characterized in that the strip has a stationary phase of a fiber chromatography material in a shape of a trip comprising a test line T and a control line C which are fixed thereon. The test line T is coated with TRPM8 protein antibody in a shape of a strip or a belt or TRPM8 related peptide fragments antibody, and the control line C is coated with IgG antibody in a shape of a strip or a belt. The TRPM8 related antibody of the test sample has a specific immune response on the test line T, and other free substances of the samples to be tested has immune responses on the control line C. The amino acid sequences of the TRPM8 protein related peptide fragments are as shown in SEQ ID No: 1-18.

The present invention also discloses a TRPM8 protein, TRPM8 related polypeptide fragments and corresponding antibodies in the preparation of the treatment of chronic prostatitis/chronic pelvic pain syndromes (CP/CPPS). The amino acid sequences of the TRPM8 protein related peptide fragments are as shown in SEQ ID No: 1-18. Any TRPM8 protein, TRPM8 related polypeptide fragments and its monoclonal antibody and polyclonal antibody prepared by any species or synthesized by genetic engineering can be utilized by an immunological method.

Specifically, TRPM8 protein or related polypeptide fragments is injected with a dosage of 1-30000 IU by intravenous or subcutaneous, so as to perform desensitization treatment, in such a manner that clinical feature of chronic prostatitis and pelvic pain syndrome is significantly cured; and monoclonal or polyclonal antibodies of TRPM8 protein or related polypeptide fragments is injected with a dosage of 1-30000 IU by intravenous or subcutaneous, in such a manner that clinical feature of chronic prostatitis and pelvic pain syndrome is significantly cured.

Beneficial effects of the present invention are as follows.

1. The present invention discloses the application of TRPM8 protein, TRPM8 related peptide fragment and corresponding antibody in preparing diagnostic reagent for chronic prostatitis/chronic pelvic pain syndromes, (CP/CPPS). By detecting the level of TRPM8 protein molecular, TRPM8 related peptide fragment and the antibody or their antibodies, so as to effectively diagnose chronic prostatitis/chronic pelvic pain syndromes, (CP/CPPS) and effectively distinguish other prostatosis.

2. The present invention further discloses the application of TRPM8 protein, TRPM8 related peptide fragment and corresponding antibody in preparing medicine for treating chronic prostatitis/chronic pelvic pain syndromes, (CP/CPPS). Applying 1~30000 IU TRPM8 protein, related peptide fragment or its monoclonal antibody or polyclonal antibody with or without combining nanoparticles by intravenous injection or subcutaneous injection is capable of curing or soothing symptoms of the chronic prostatitis/chronic pelvic pain syndromes, (CP/CPPS).

These and other objectives, features, and advantages of the present invention will become apparent from the following detailed description, the accompanying drawings, and the appended claims.

DETAILED DESCRIPTION OF THE PREFERRED EMBODIMENT

Embodiment 1

Preparation of TRPM8 Related Peptide Fragment

Figure 1:
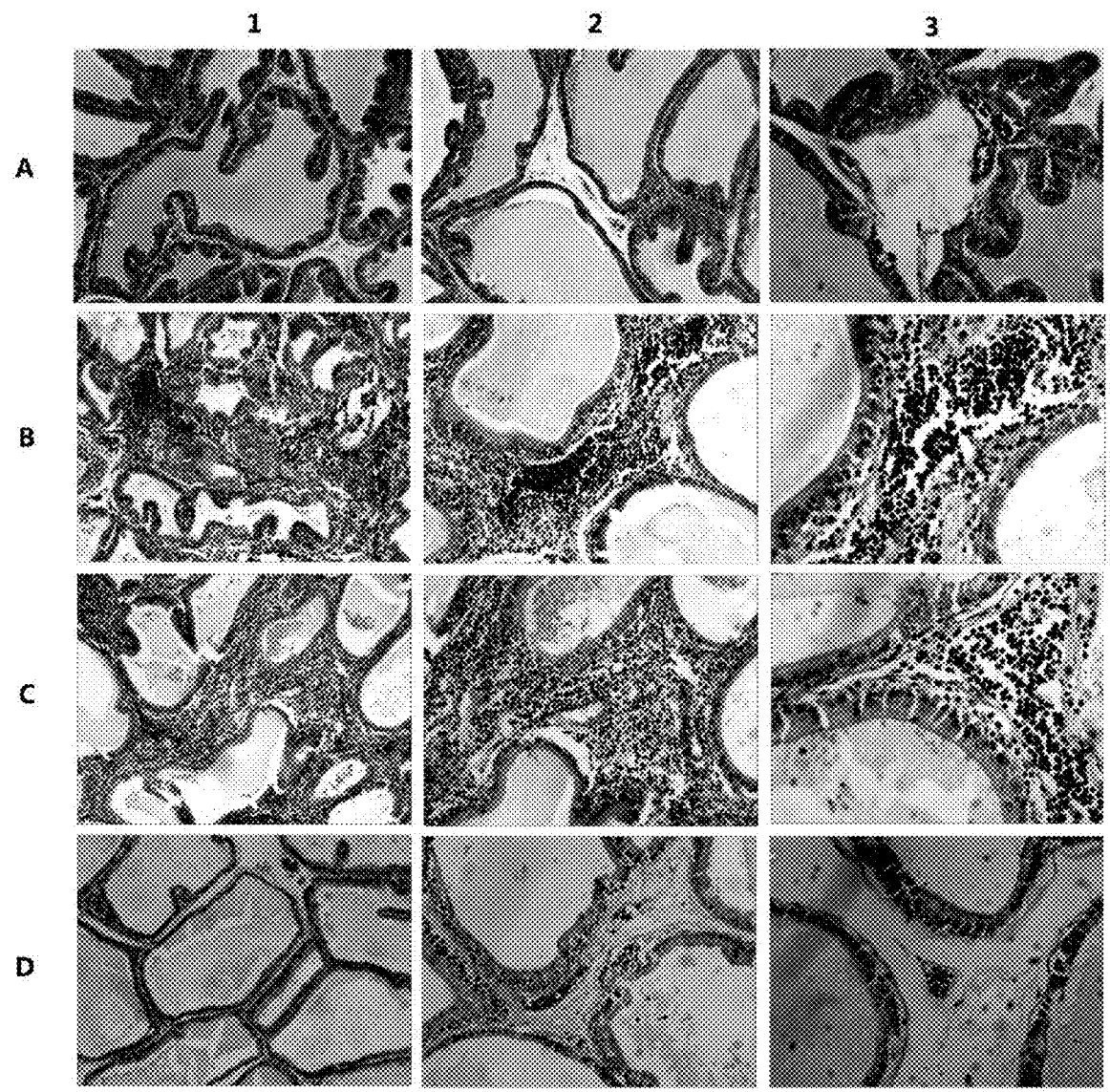
FIG. 1 is an HE staining result of each group of prostate pathological section.

From transmembrane analysis of TRPM8, following sections are positioned outside the membrane: 1-692, 758-796, 849-862, 916-953 and 1025-1104. From a comprehensive analysis of various kinds of software, 18 extracellular fragments of transmembrane protein are finally chosen, and the chosen amino acid sequence substantially covered extracellular fragments fully, which is:

T-1: Biotin-KINTKANDTSEEMRHRFRQLDTKLND (26AA); wherein "Biotin-" represents that sequence of KINTKANDTSEEMRHRFRQLDTKLND is capable of combining with Biotin, i.e., Vitamin H, so as to form a stable structure, hereafter inclusive. T-2: Biotin-FKNEDNET-LAWEGVMKENYL (20AA);

```
T-3: Biotin-DGTTYDFAHCTFTGNESKPL (20AA);

T-4: Biotin-VSRNLGPKIIMLQ (13AA);

T-5: Biotin-DEVRQWYVNGVNYFTD (16AA);

T-6: Biotin-LTVIKMEEAGDEIVSNA (17AA).

T-7: CKEKN MESSY CCFKN EDNET

T-8: CSEEM RHRFR QLDTK LNDLKG

T-9: CFTGNE SKPLCV ELDEH NLPRFPE

T-10: NRRND TLDST RTLYSS

T-11: VEVED ALTSS AVKEK LVRFC

T-12: CEMDI ELHDV SPITRH

T-13: KEKNMESSVCCFKNEDNET

T-14: SEEMRHRFRQLDTKLNDLKG

T-15: FTGNESKPLCVELDEHNLPRFPE

T-16: NRRNDTLDSTRTLYSSASRSTDLSYS

T-17: VEVEDALTSSAVKEKLVRF

T-18: EMDIELHDVSPITRH
```

The peptide fragment mentioned above is synthesized by bioyeargene biological technology co., LTD. The TRPM8 was purchased from ProteinTech Group.

Embodiment 2

Antigenicity Detection of TRPM8 Protein and TRPM8 Related Peptide Fragment

In order to prove that TRPM8 protein is the key to CP/CPPS induction and antigen pathogenicity of TRPM8 related peptide fragment. Experiment is designed and performed as follows. Firstly, pure TRPM8 protein is combined with Complete Freund's adjuvant (CFA) to establish an animal model of CP/CPPS. The animal model is compared with a prostatein homogenate modeling method. Meanwhile, TRPM8 in prostatein homogenate is removed by immunomagnetic beads; wherein the prostatein homogenate is molded for serving as a negative control. HE staining method is utilized to evaluate the severity of inflammation in prostate tissue of each modeling group of animal, and the severity of inflammation in prostate tissue is performed with pathological score. CD3 immunofluorescence method is adopted to observe infiltrating of T lymphocyte in prostate of the modeling animal.

Take 40 8-week-old SPF level male SD rats, with weights at a range of 250±20 g. The rats are purchased from Shanghai Sijie laboratory Co., Ltd with a license number of SCXK (Shanghai) 2012-0006. Under an aseptic condition, prostate of an SD rats is taken to prepare prostatein homogenate and TRPM8 removed homogenate protein. Grouping of immune animals in experiments is as follows. 40 8-week-old SD rats are randomly classified into 4 groups, i.e., a homogenate protein group, a TRPM8 removed homogenate protein group, a pure TRPM8 protein group and a control group; wherein each group comprises 10 rats. After 8 weeks of immune, each group of the rats are injected with 10% chloral hydrate on abdomen for anesthesia, and plasma and prostate of each group of rats are respectively collected. Preparation of prostate pathological section: the paraffin embedded prostate sections of the rats in each experimental group are sent to a drying oven, heated under 60° C. for 30 min. Then according to the conventional method, the prostate pathological sections are sent to each staining jar, dewaxed by dimethylbenzene, hydrated by gradient ethanol, stained by hematoxylin-and-eosin-stain, dehydrated by gradient ethanol and hyalinized by xylene. The prostate pathological sections are covered by neutral resin and then observed and photographed under a microscope. The covered prostate pathological sections are preserved under 4° C.

In addition, the prostate tissue sections of each group of animals to be tested are taken, baked in an oven for 30 minutes at 60° C., then subjected to CD3 immunofluorescence, and finally added with anti-fluorescence quenching agent for sealing, observed under a microscope, wherein photos are taken.

According to the method mentioned above, TRPM8 protein related peptide fragments are adopted to immune rats, so as to produce corresponding prostate tissue sections.

Group T-1 is corresponding to a TRPM8 related peptide fragment: Biotin-KINTKANDTSEEMRHR-FRQLDTKLND (SEQ ID: No 1): wherein "Biotin-" represents that sequence of KINTKANDTSEEMRHR-FRQLDTKLND is capable of combining with Biotin, i.e., Vitamin H, so as to form a stable structure, hereafter inclusive.

Group T-2 is corresponding to a TRPM8 related peptide fragment: Biotin-FKNEDNETLAWEGVMKENYL, (SEQ ID: No 2);

Group T-3 is corresponding to a TRPM8 related peptide fragment: Biotin-DGTTYDFAHCTFTGNESKPL (SEQ ID: No 3);

Group T-4 is corresponding to a TRPM8 related peptide fragment: Biotin-VSRNLGPKIIMLQ (SEQ ID: No 4);

Group T-5 is corresponding to a TRPM8 related peptide fragment: Biotin-DEVRQWYVNGVNYFTD (SEQ ID: No 5);

Group T-6 is corresponding to a TRPM8 related peptide fragment: Biotin-LTVIKMEEAGDEIVSNA (SEQ ID: No 6).

Group T-7 is corresponding to a TRPM8 related peptide fragment CKEKN MESSV CCFKN EDNET (SEQ ID: No 7).

Group T-8 is corresponding to a TRPM8 related peptide fragment CSEEM RHRFR QLDTK LNDLKG (SEQ ID: No 8).

Group T-9 is corresponding to a TRPM8 related peptide fragment CFTGNE SKPLCV ELDEH NLPRFPE (SEQ ID: No 9).

Group T-10 is corresponding to a TRPM8 related peptide fragment NRRND TLDST RTLYSS (SEQ ID: No 10).

Group T-11 is corresponding to a TRPM8 related peptide fragment VEVED ALTSS AVKEK LVRFC (SEQ ID: No 11).

Group T-12 is corresponding to a TRPM8 related peptide fragment CEMDI ELHDV SPITRH (SEQ ID: No 12).

Group T-13 is corresponding to a TRPM8 related peptide fragment KEKNMESSVCCFKNEDNET (SEQ ID: No 13).

Group T-14 is corresponding to a TRPM8 related peptide fragment SEEMRHRFRQLDTKLNDLKG (SEQ ID: No 14).

Group T-15 is corresponding to a TRPM8 related peptide fragment FTGNESKPLCVELDEHNLPRFPE (SEQ ID: No 15).

Group T-16 is corresponding to a TRPM8 related peptide fragment NRRNDTLDSTRTLYSSASRSTDLSYS (SEQ ID: No 16).

Group T-17 is corresponding to a TRPM8 related peptide fragment VEVEDALTSSAVKEKLVRF (SEQ ID: No 17).

Group T-18 is corresponding to a TRPM8 related peptide fragment EMDIELHDVSPITRH (SEQ ID: No 18).

Control group: blank control group.

According to HE staining result, prostatitis degree of each group of rats are pathologically scored under standards as follows.

Score 0: Without any inflammatory cell infiltration and without any signs of inflammation;

Score 1: A small amount of acinar epithelial shrinks;

Score 2: A plurality of acinar epithelial shrinks and a small amount of inflammatory cell infiltration;

Score 3: Severely shrinks of acinar epithelial, severe congestion in the prostate body and a plurality of inflammatory cell infiltration.

Each prostate section is scored by three associate professors in pathology according to the standards mentioned above under a randomized and double-blind principle, and an average value calculated is a histological score indicating degree of the prostatitis of the animal.

Statistical analysis was performed using excel 2007, average values of the pathological evaluation indicating the degree of the prostatitis of the animal is performed with homogeneity test of variance and one-way analysis of variance (One-Way ANOVA). $p<0.05$: there is a significant difference; $p<0.01$ there is a highly significant difference.

HE Staining and Pathological Valuation Result

Figure 2:
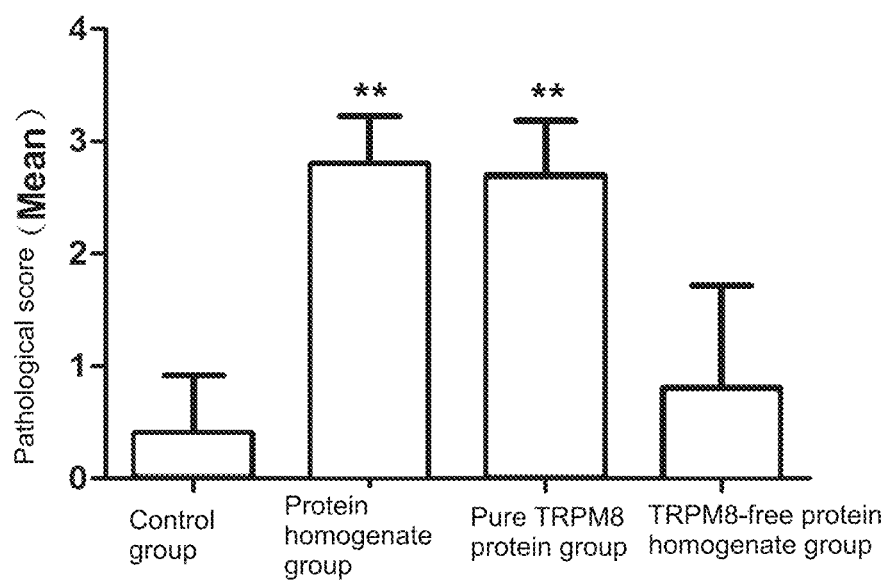
FIG. 2 is a pathological evaluation result of each group of prostate tissue. (**$p<0.01$ VS control group).

Referring to FIG. 1, (1: under a 10× objective lens; 2: under a 20× objective lens; 3: under a 40× objective lens; B: protein homogenate group; C: pure TRPM8 protein group; D protein homogenate group; TRPM8 protein-free homogenate group) and FIG. 2, a plurality of inflammatory cell infiltration is seen in prostate stromal of all animals in the protein homogenate group, severe congestion appears in gland. An average value of the histological score is 2.7778±0.4410 (M±SD), which is also much lower than the protein homogenate modeling group.

In order to research that whether the effect of inducing CP/CPPS morbidity is caused by the TRPM8 in prostatein homogenate, the TRPM8 protein is removed from protein homogenate by immunomagnetic beads method. The result shows that in the TRPM8 protein-free homogenate combining with CFA modeling group, pathophysiological changes of the prostate and the inflammatory cell infiltration are greatly decreased. The histological score (0.8000±0.9190)

indicates that level of prostatitis in animals of the TRPM8 protein-free group does not have a significant difference compared with the control blank group.

In addition, pure TRPM8 protein is combined with CFA for immuring SD rat, so as to further verify the effects of TRPM8 protein in CP/CPPS morbidity. FIG. 1 shows that TRPM8 protein successfully induces generation of CP/CPPS. There is serious congestion in the prostate, and there is a plurality of inflammatory cell infiltration in mesenchyme and particularly around blood vessels. The pathological evaluation (2.7000±0.4830) is very close to the protein homogenate.

2. Immunofluorescence Staining Results of CD3

Figure 3:
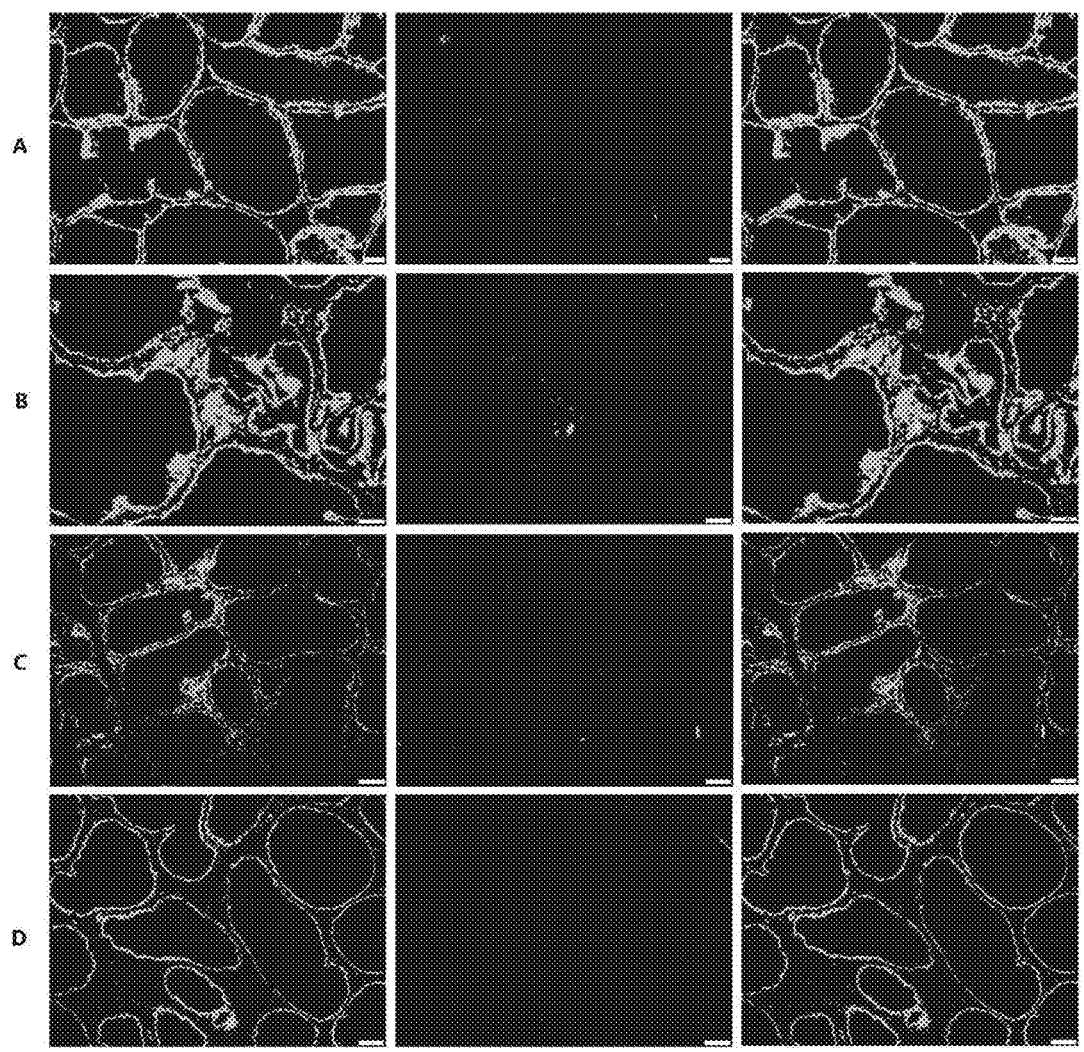
FIG. 3 is a CD3 immunofluorescence staining result of each group of prostate tissue.

Seen from HE staining results, prostate tissue of rats in the protein homogenate group and the pure TRPM8 protein group has a plurality of inflammatory cell infiltration. In order to improve the inflammatory cell containing a plurality of T-lymphocytes, the CD3 molecules are performed with immunofluorescence staining. The results are shown in FIG. 3: A: control blank group; B: protein homogenate group; C: pure TRPM8 protein group; D: TRPM8 protein free homogenate group. A large area of CD3 molecule marked by red luminescence can be seen in prostate mesenchyme, which indicates that most of the infiltrative inflammatory cells are T-lymphocytes, not innate immune cells such as neutrophils or macrophages. However, in the blank control group and the TRPM8 protein-free homogenate group, there is almost no inflammatory cell infiltration in the prostate stromal, and the immunofluorescence staining is negative, indicating that no T lymphocyte is in the prostate stromal.

Figure 4:
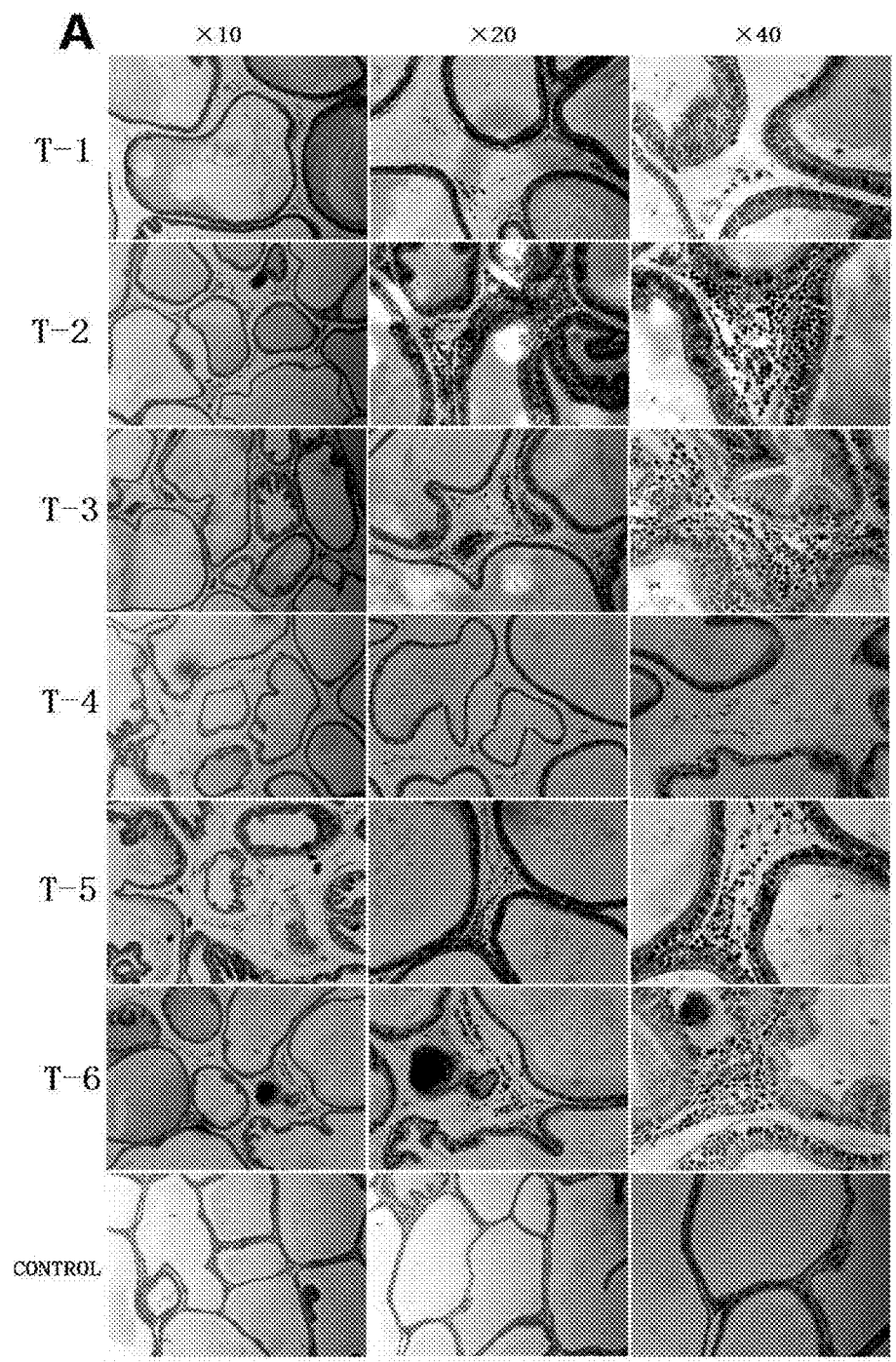
FIG. 4 is a HE staining result of each group of prostate pathological section after adopting TRPM8 related peptide fragment.
Figure 5:
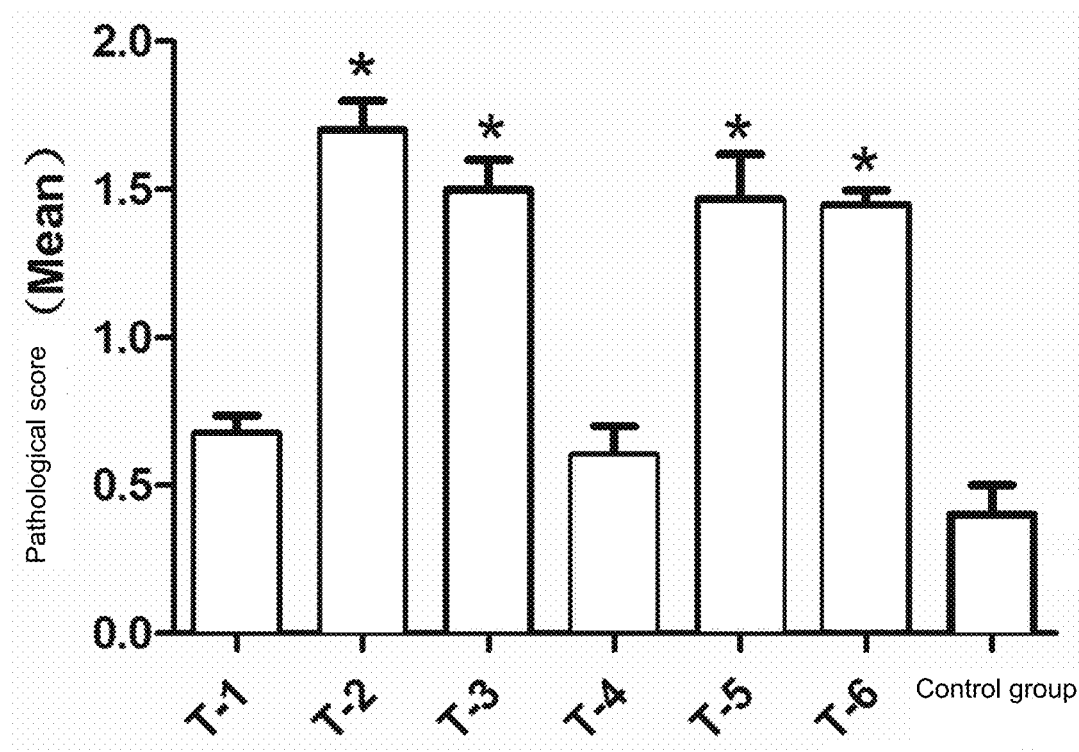
FIG. 5 is a pathological evaluation result of each group of prostate tissue after adopting TRPM8 related peptide fragment. (**$p<0.01$ VS control group).

Testing results of antigen pathogenicity of TRPM8 and related peptide fragment are as shown in FIG. 4 and FIG. 5. Experimental results of studies of antigen pathogenicity of TRPM8 related peptide fragment indicate that all TRPM8 related peptide fragments show strong pathogenicity causing CP/CPPS.

In summary, both the TRPM8 protein and the TRPM8 related peptide fragment have strong pathogenicity causing CP/CPPS.

Embodiment 3

(I) Preparation of TRPM8 Protein and TRPM8 Related Peptide Fragments

Animal Selection and Immunization

1. Animal selection: pure BALB/C mice.
2. Immunization programs

Selecting an appropriate immunization program is essential for success of cell fusion and hybridization and obtaining high quality McAb. Usually, primary immunization is started according to the immunization program two month before the fusion. The immunization program is determined based on different characteristics of the antigen.

Complete sequence of human-derived TRPM8 protein and peptide fragment as shown in SEQ ID No: 1-6 are selected for serving as antigen. Freund's adjuvant is adopted for respectively immunizing the mice.

1-50 µg of primary immune antigen adding with freund's complete adjuvant is applied to the mice by multiple sites subcutaneous injection or spleen injection (usually 0.8~1 ml, 0.2 ml/site. After 3 weeks, a secondary immunization is performed by an identical dosage as mentioned above, incomplete Freund's adjuvant subcutaneously or ip (intraperitoneal injection) (ip dose should not exceed 0.5 ml). Three weeks after the third immunization is performed with an identical dose, without adjuvant, (5-7 days after, blood is collected for testing its potency). 2 to 3 weeks after, enhancing the immune by a dosage of 500 µg is appropriate, intravenously, three days later, performing spleen integration.

(II) Cell Fusion

1. Preparation before cell fusion (1) Selection of myeloma cell line

The myeloma cells are derived from mice. Inoculating hybridoma on abdominal cavity of the same strains of mice, and a plurality of McAb is generated.

(2) Feeder cells

In tissue culture, adding feeder cells comprises mice peritoneal macrophage. An amount of the feeder cell is $2\times10^4$ or $10^5$ per pore.

2. The cell fusion comprises steps as follows:

(1) preparing feeder layer cell comprising: selecting mice peritoneal macrophage, adopting 6-10 week old BALB/C mice which is in an identical stain with the immune mice, necking, killing, immersing in 75% ethyl alcohol for 3-5 min, cutting skins of the mice by sterile scissors to expose peritoneum, injecting 5-6 ml pre-cooling nutrient solution by a sterile syringe (strictly forbidding piercing intestinal canal, washing repeatedly, extracting flushing fluid, sending the flushing fluid into 10 ml centrifuge tube, centrifuging for 5-6 min under 1200 rpm, suspending in nutrient solution of 20% calf serum (NCS) or fetal calf serum (FCS), regulating cell number to $1\times10^5$/ml, adding 100 µl/pore to a 96 pore plate, and sending to a $CO_2$ incubator culturing under 37° C.;

(2) preparing immunized splenic cells after booster immunization for 3 days, necking the mice for killing, taking spleen under sterile conditions, washing by nutrient solution, grinding the spleen, passing through a cell strainer, centrifuging, washing the cell twice by nutrient solution, counting and taking $10^8$ splenic lymphocyte suspension for reserving;

(3) preparing myeloma cell taking logarithmic growth myeloma cell, centrifuging, washing twice by serum free nutrient solution, counting to obtain $\times10^7$ cells for reserving;

(4) fusing

① mixing myeloma cells and splenic cells according to a proportion of 1:10 or 1:5, washing once in a serum-free culture solution in a 50 ml centrifuge tube, centrifuging under 1200 rpm for 8 min; abandoning supernatant, sucking all residual liquid with a pipette, so as to prevent affecting concentration of polyethylene glycol (PEG), gently flicking a bottom of the 50 ml centrifuge tube, so as to make cell deposition become more loose;

② adding 1 ml 45% PEG solution which is preheated at 37° C. and with a molecular weight of 4000 in 90 s into the centrifuge tube, slightly shaking the centrifuge tube while adding the PEG solution, and keeping in a 37° C. water bath for 90 s;

③ adding a 37° C. preheated incomplete culture solution to terminate PEG effects, wherein the incomplete culture solution is respectively added with dosages of 1 ml, 2 ml, 3 ml, 4 ml, 5 ml and 6 ml at each two-minute interval;

④ centrifuging under 800 rpm for 6 min;

⑤ taking the supernatant to be re-suspended utilizing HAT selection culture solution containing 20% calf serum;

⑥ adding the cells mentioned above to a 96-pore plate with an existing feeder cell layer, adding 100 µl for each pore; wherein usually one immune spleen can be inoculated on 4 pieces of 96-pore plate; and ⑦ sending the 96-pore plate to an incubator at 37° C. with 5% $CO_2$.

(III) Selection of Hybridoma Cells and Test of Antibodies

1. HAT selection of hybridoma cell comprises steps of:

PEG treating spleen cells and myeloma cells to form a mixture of a variety of cells, wherein only the hybridoma cells formed by the spleen cells and myeloma cells are selected;

wherein during the process of culturing in HAGT selection solution, since the myeloma cells lack thymidine kinase or hypoxanthine-guanine phosphoribosyltransferase, and the myeloma cells are not capable of growing and reproducing; the hybridoma cells have the thymidine kinase or hypoxanthine-guanine phosphoribosyltransferase and thus are capable of growing and reproducing in HAT selection culture solution;

wherein in 1-2 days of HAT selection culture, a large amount of cells are died, after 3-4 days tumor cells disappear and the hybrid cells form small colonies, maintaining the HAT selection culture solution for 7-10 days and then the HAT selection culture solution is changed to HT culture solution, maintain for 2 weeks and conventional culture solution is changed; during the selection culture period, when the hybridoma cells cover 1/10 area of a pore bottom, specific antibodies are detected to select required hybridoma cell lines; wherein during the process of selection culture, half of the culture solution is changed in every 2-3 days.

2. Detection of TRPM8 antibody: utilizing a radioimmunoassay (RIA) method.

(IV) Hybridoma Clone

The present invention utilizes a limited dilution clone method comprising steps of:

(1) preparing a feeder cell layer one day before clone, which is identical to cell fusion;

(2) blow-drying hybridoma to be cloned in the culture hole and counting;

(3) regulating the cells to a density of 3-10/ml;

(4) taking a cell culture plate in which the feeder cell layer is cultured, adding 100 ml dilution cells in each pore to be incubated at an incubator at 37° C. and with 5% $CO_2$;

(5) changing liquid in the seventh day, wherein the liquid is changed in every 2-3 days;

(6) in 8-9 days, when clone cells are formed, timely detecting activity of the antibody;

(7) moving cells in positive holes to a 24-pore plate for expanded culture; and (8) frozen preserving each clone as soon as possible.

(V) Frozen Preservation and Recovery of Hybridoma Cell (1) Cryopreservation of hybridoma cells cryopreservation solution: 50% fetal bovine serum; 40% incomplete culture solution and 10% DMSO (dimethyl sulfoxide).

The cryopreservation solution is preferably cooled, wherein cooling operation is gentle and fast, wherein during the cryopreservation process, temperature is dropped from a room temperature to 0° C. and immediately sent to an ultra-low temperature freezer, and then converted to liquid nitrogen the next day.

(2) Cell recovery method comprising steps of:

taking glass ampoule from liquid nitrogen carefully, putting in a water bath at 37° C., unfreezing frozen cells, washing the cells twice with completed culture solution, and sending to a cell flask for feeder layer prepared one-day before, sending to an incubator at 37° C. and with 5% $CO_2$ for culturing, when the cells form colonies, detecting activity of the antibody.

(VI) Mass Production of Monoclonal Antibodies

The present invention adopts a solid tumor method comprising:

incubating logarithmic phase hybridoma cells by 1-3× $10^7$/ml subcutaneously in the back of a mice, injecting 0.2 ml at each site for a total of 2-4 sites, when the tumor reaches a certain size, generally after 10 to 20 days, blood sampling, wherein serum obtained from the monoclonal antibody content can reach 1-10 mg/ml.

Antibody Identification

TABLE 3

|      | Dosage | Specificity | Affinity | Valence |
| --- | --- | --- | --- | --- |
| TRPM8 | 1 μg  | High | $10^{12}$ L/mol | 1:128 |
| T-1  | 35 ng | High | $10^{12}$ L/mol | 1:128 |
| T-2  | 35 ng | High | $10^{12}$ L/mol | 1:128 |
| T-3  | 35 ng | High | $10^{12}$ L/mol | 1:128 |
| T-4  | 35 ng | High | $10^{12}$ L/mol | 1:128 |
| T-5  | 35 ng | High | $10^{12}$ L/mol | 1:128 |
| T-6  | 35 ng | High | $10^{12}$ L/mol | 1:128 |
| T-7  | 35 ng | High | $10^{12}$ L/mol | 1:128 |
| T-8  | 35 ng | High | $10^{12}$ L/mol | 1:128 |
| T-9  | 35 ng | High | $10^{12}$ L/mol | 1:128 |
| T-10 | 35 ng | High | $10^{12}$ L/mol | 1:128 |
| T-11 | 35 ng | High | $10^{12}$ L/mol | 1:128 |
| T-12 | 35 ng | High | $10^{12}$ L/mol | 1:128 |
| T-13 | 35 ng | High | $10^{12}$ L/mol | 1:128 |
| T-14 | 35 ng | High | $10^{12}$ L/mol | 1:128 |
| T-15 | 35 ng | High | $10^{12}$ L/mol | 1:128 |
| T-16 | 35 ng | High | $10^{12}$ L/mol | 1:128 |
| T-17 | 35 ng | High | $10^{12}$ L/mol | 1:128 |
| T-18 | 35 ng | High | $10^{12}$ L/mol | 1:128 |

Embodiment 4

ELISA diagnostic kit for chronic prostatitis or chronic pelvic pain syndrome, comprising:

(1) TRPM8 protein which is coated (1 μg) or solid carrier of TRPM8-related polypeptide fragment (35 ng), solid carrier coated by anti-human IgG antibody (1 μg) and enzyme marked TRPM8 protein antibody or antibody TRPM8 protein related peptide fragments (1 μg), wherein amino acid sequences of the TRPM8 protein related peptide fragments are as shown in SEQ ID No: 1-18 below;

(2) substrate for the enzyme;

(3) negative control, positive control and/or reference standards and control serum, 0.5 ml in each;

(4) 1.0 m conjugate and 1.0 ml dilution of the respective samples 1;

(5) 5 ml washing solution;

(6) 2 ml enzyme reaction terminated liquid.

60 clinical persons are tested. Utilizing the kit of the TRPM8 and TRPM8 related peptide fragments to detect plasma of the persons who are tested, comprising 15 healthy persons, 15 clinically diagnosed CP/CPPS patients, 15 bacterial prostatitis patients, 15 prostatic cancer patients, so as to verify the accuracy rate of the kit of the present invention. The results are as shown in Table. 5, wherein testing values of 12 of the 15 bacterial prostatitis patients are smaller than 10 ng/ml and the elimination rate is 80%; testing values of the 15 prostatic cancer patients are all greater than 500 ng/ml, and the elimination rate is 100%. Thus, it can be seen that the kit of the present invention is capable of effectively diagnosing the CP/CPPS patients and effectively identifying CP/CPPS and other protastic disorders such as bacterial prostatitis and prostatic cancer.

TABLE 4

Diagnostic Criteria

| Detection group | Detection value of TRPM8 protein or related peptide fragment (ng/ml) | Antibody detection value of TRPM8 protein or related peptide fragment (ng/ml) |
| --- | --- | --- |
| Chronic prostatitis or chronic pelvic pain syndrome | 10 ≤ detection value < 200, judged positive CP/CPPS | 250 ≤ detection value < 500, judged positive CP/CPPS |
| Normal individuals | Detection value < 10, judged negative CP/CPPS | Detection value < 5, judged negative CP/CPPS |
| Bacterial prostatitis | <10 | <5 |
| Prostate cancer | ≥500 | ≥2000 |

TABLE 5

| | | Plasma samples | |
| --- | --- | --- | --- |
| | | TRPM8 protein detection accuracy | TRPM8 antibody detection accuracy |
| TRPM8 | Normal human beings | 100% (15 human beings negative) | 100% (15 human beings negative) |
| | CP/CPPS patient | 86.67% (13 human beings positive) | 86.67% (13 human beings positive) |
| T-1 | Normal human beings | 100% (15 human beings negative) | 100% (15 human beings negative) |
| | CP/CPPS patient | 86.67% (13 human beings positive) | 86.67% (13 human beings positive) |
| T-3 | Normal human beings | 100% (15 human beings negative) | 100% (15 human beings negative) |
| | CP/CPPS patient | 86.67% (13 human beings positive) | 86.67% (13 human beings positive) |
| T-6 | Normal human beings | 100% (15 human beings negative) | 100% (15 human beings negative) |
| | CP/CPPS patient | 86.67% (13 human beings positive) | 86.67% (13 human beings positive) |
| T-9 | Normal human beings | 100% (15 human beings negative) | 100% (15 human beings negative) |
| | CP/CPPS patient | 86.67% (13 human beings positive) | 86.67% (13 human beings positive) |
| T-15 | Normal human beings | 100% (15 human beings negative) | 100% (15 human beings negative) |
| | CP/CPPS patient | 86.67% (13 human beings positive) | 86.67% (13 human beings positive) |
| T-18 | Normal human beings | 100% (15 human beings negative) | 100% (15 human beings negative) |
| | CP/CPPS patient | 86.67% (13 human beings positive) | 86.67% (13 human beings positive) |

Embodiment 5

A Test Strip for Diagnosis of Chronic Prostatitis/Chronic Pelvic Pain Syndromes (CP/CPPS)

In a homogeneous immunological method, for example, specific methods are: respectively pasting an NC film, an absorbent pad, a conjugate pad sprayed with fluorescent-labeled antibody and glass fiber which is infiltrated in developing solvent and then dried, in such a manner that an immuno-chromatographic strip is assembled. TRPM8 protein or TRPM8 related polypeptide fragments with a concentration of 10 ng/kg are evenly sprayed on the NC film by a non-contact micro-sprinkler on a three-dimensional spraying platform to form 2 lines with a moderate thickness in parallel including a non-contact micro-sprinkler T line for coating antigen and a C line of goat anti human/rat with a concentration of 10 ng/kg and a dosage of 100 ul;

putting the immuno-chromatographic strip in an incubator to keep 37° C. for 1 h and taking out; cutting the immuno-chromatographic strip into a plurality of paper slips with a size at a range of 4 mm±2 mm, and sending the plurality of paper slips to an aluminum foil bag with desiccant for a sealed preservation;

dropping liquid to be detected on an appropriate position of the test trip, performing chromatography, shooting and detecting under a characteristic excitation wave length of 320 nm and an emission wavelength of 620 nm;

performing sensitivity, specificity and simulation of positive samples according to the method mentioned above;

wherein when the samples to be detected is siphoned from bottom to top along the paper slip by capillary action, according to chromatographic theory, the samples to be detected is moved from a detecting end of the paper slip to the other end of the paper slip, wherein the samples to be detected respectively passes through the conjugate pad, the NC film, the T line and the C line to reach the absorbent pad.

After the chromatography, if the C line is not colored, the paper strip is considered invalid; if the C line develops color, the paper strip is considered valid; if the C line develops colors but the T line is not colored, the test result is positive; if both the T line and the C line develop color, the test result is negative.

TABLE 6

| Morbidity situation | TRPM8 protein humor detection results | TRPM8 antibody humor detection result |
| --- | --- | --- |
| Patients of chronic prostatitis or chronic pelvic pain syndrome | Positive (both C line and T line are developed) | Positive (both C line and T line are developed) |
| Normal human beings | Negative (C line developed, T line not developed) | Negative (C line developed, T line not developed) |

Invalid: ribbon does not appear on the quality control region (C), indicating that operation procedure is incorrect or the reagent strip has gone corrupt, re-testing is performed.

Note: The test strip control line and test line ribbon may appear light or dark color due to the contents of TRPM8 or TRPM8 antibody in body fluids, the result is determined according to the above criteria. For insurance purposes, the test is performed again after three days.

Embodiment 6

Therapeutic Effect of TRPM8 Protein and TRPM8 Related Polypeptide Antibodies in Treatment of Chronic Prostatitis/Chronic Pelvic Pain Syndromes (CP/CPPS).

Implementation

Respectively prepare monoclonal antibody of TRPM8 protein and TRPM8 related peptide, perform intravenous subcutaneous injection by 1-30000 IU for once a day, and 14 days are a course of treatment, wherein the relationships between the using dosage and the clinical manifestation are as shown in Table. 7.

TABLE 7

| Condition of chronic prostatitis/chronic pelvic pain syndromes, CP/CPPS | Application monoclonal antibody of TRPM8 and TRPM8 related peptide TRPM8 (IU) | Clinical improvement indicators of patients |
| --- | --- | --- |
| Mild | 1000~10000 IU, once a day, intravenous injection | Symptoms improved; TRPM8 humoral antibody detection value <5 |

TABLE 7-continued

| Condition of chronic prostatitis/chronic pelvic pain syndromes, CP/CPPS | Application monoclonal antibody of TRPM8 and TRPM8 related peptide TRPM8 (IU) | Clinical improvement indicators of patients |
| --- | --- | --- |
| Moderate | 2000~20000 IU, once a day, intravenous injection | ng/ml; TRPM8 protein in body fluids to detect the value <10 ng/ml; prostatic fluid leukocytes <5/HPF; Ultrasonic B-show normal prostate volume and structure. |
| Severe | 3000~30000 IU or above, once a day, intravenous injection | |

The results are shown in Table 8; the results show that TRPM8 and TRPM8 related polypeptide monoclonal antibodies may be effective in curing or alleviating chronic prostatitis or chronic pelvic pain syndrome.

TABLE 8

| | Dosage and administration | Patient number in group | Cure rate (%) | Efficiency rate (%) | Effective rate (%) | Ineffective rate (%) |
| --- | --- | --- | --- | --- | --- | --- |
| Negative control: hepgarin | 2000 IU, once a day, intravenous injection | 100 | 0 | 0 | 0 | 100 |
| Positive control medicine: Qianliekang | Four pills at a time, 3 times a day, by oral administration | 100 | 60 | 10 | 70 | 30 |
| TRPM8 monoclonal antibody | 10000 IU, once a day, intravenous injection | 100 | 62 | 10 | 72 | 28 |
| T-1 monoclonal antibody | 15000 IU, once a day, intravenous injection | 100 | 61 | 20 | 82 | 18 |
| T-6 monoclonal antibody | 13000 IU, once a day, intravenous injection | 100 | 62 | 30 | 92 | 8 |
| T-9 monoclonal antibody | 6000 IU, once a day, intravenous injection | 100 | 92 | 5 | 97 | 3 |
| T-12 monoclonal antibody | 8000 IU, once a day, intravenous injection | 100 | 83 | 12 | 95 | 5 |
| T-15 monoclonal antibody | 9000 IU, once a day, intravenous injection | 100 | 81 | 10 | 91 | 9 |
| T-18 monoclonal antibody | 9600 IU, once a day, intravenous injection | 100 | 88 | 5 | 93 | 7 |

Embodiment 7

The Therapeutic Action of TRPM8 Protein and TRPM8 Related Polypeptides Desensitization Therapy for Chronic Prostatitis or Chronic Pelvic Pain Syndrome TRPM8 protein and TRPM8 related polypeptide are respectively prepared. By injecting 1-30000 units by intravenous or subcutaneous once a day, each course comprises 14 days. The relationships between the application dosage and the clinical manifestation are as shown in Table. 9.

TABLE 9

| Condition of chronic prostatitis/chronic pelvic pain syndromes, CP/CPPS | Application of monoclonal antibody of TRPM8 and TRPM8 related peptide TRPM8 (IU) | Clinical improvement indicators of patients |
| --- | --- | --- |
| Mild | 1~10000 IU, once a day, intravenous injection | Symptoms improved; TRPM8 humoral antibody detection value <5 |
| Moderate | 2000~20000 IU, once a day, intravenous injection | ng/ml; TRPM8 protein in body fluids to detect the value <10 ng/ml; |

TABLE 9-continued

| Condition of chronic prostatitis/chronic pelvic pain syndromes, CP/CPPS | Application of monoclonal antibody of TRPM8 and TRPM8 related peptide TRPM8 (IU) | Clinical improvement indicators of patients |
|---|---|---|
| Severe | 3000~30000 IU or above, once a day, intravenous injection | prostatic fluid leukocytes <5/HPF; Ultrasonic B-show normal prostate volume and structure. |

The results are shown in Table 10. The results show that TRPM8 and TRPM8 polypeptide associated desensitization therapy can be effective in curing or alleviating chronic prostatitis or chronic pelvic pain syndrome.

TABLE 10

| | Dosage and administration | Patient number in group | Cure rate (%) | Efficiency rate (%) | Effective rate (%) | Ineffective rate (%) |
|---|---|---|---|---|---|---|
| Negative control: hepgarin | 2000 IU, once a day, intravenous injection | 100 | 0 | 0 | 0 | 100 |
| Positive control medicine: Qianliekang | Four pills at a time, 3 times a day, by oral administration | 100 | 60 | 10 | 70 | 30 |
| TRPM8 monoclonal antibody | 10000 IU, once a day, intravenous injection | 100 | 62 | 10 | 72 | 28 |
| T-1 monoclonal antibody | 15000 IU, once a day, intravenous injection | 100 | 61 | 20 | 82 | 18 |
| T-6 monoclonal antibody | 13000 IU, once a day, intravenous injection | 100 | 62 | 30 | 92 | 8 |
| T-9 monoclonal antibody | 6000 IU, once a day, intravenous injection | 100 | 92 | 5 | 97 | 3 |
| T-12 monoclonal antibody | 8000 IU, once a day, intravenous injection | 100 | 83 | 12 | 95 | 5 |
| T-15 monoclonal antibody | 9000 IU, once a day, intravenous injection | 100 | 81 | 10 | 91 | 9 |
| T-18 monoclonal antibody | 9600 IU, once a day, intravenous injection | 100 | 88 | 5 | 93 | 7 |

One skilled in the art will understand that the embodiment of the present invention as shown in the drawings and described above only is exemplary and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A Transient Receptor Potential Cation Channel Subfamily M member 8 (TRPM8) related peptide fragment, comprising the amino acid sequence of SEQ ID NO:8, SEQ ID NO:9, SEQ ID NO:11, or SEQ ID NO:12.

2. The Transient Receptor Potential Cation Channel Subfamily M member 8 (TRPM8) related peptide fragment of claim 1 wherein the TRPM8 related peptide fragment is synthesized by a chemical method or by an engineering method.

3. An ELISA diagnostic kit for chronic prostatitis or chronic pelvic pain syndrome, which is characterized in comprising:
   (1) a solid phase carrier coated by the TRMP8 related peptide fragment of claim 1;
   (2) an enzyme substrate;
   (3) a negative control, either a positive control or a reference standard, and a control serum;
   (4) a composition and specimen dilution;
   (5) a washing solution; and
   (6) an enzyme reaction termination liquid.

4. A diagnosis strip for chronic prostatitis or chronic pelvic pain syndrome wherein:
   the strip is coated by the TRMP8 related peptide fragment of claim 1.

5. The ELISA diagnostic kit of claim 3, wherein the TRPM8 related peptide fragment is synthesized by a chemical method or by an engineering method.

* * * * *

UNITED STATES PATENT AND TRADEMARK OFFICE
CERTIFICATE OF CORRECTION

PATENT NO. : 11,175,289 B2
APPLICATION NO. : 15/352607
DATED : November 16, 2021
INVENTOR(S) : Xiaohui Zhou et al.

Page 1 of 1

It is certified that error appears in the above-identified patent and that said Letters Patent is hereby corrected as shown below:

On the Title Page

Item (12) delete "Lei Han et al." insert -- Xiaohui ZHOU et al. --.

Under Item (71) Applicants and Item (72) Inventors, the inventors names should read as follows:
Xiaohui ZHOU, Jiangsu (CN); Lei HAN, Jiangsu (CN); Yuyan ZHOU, Jiangsu (CN); Li ZHOU, Jiangsu (CN); Guohua LI, Jiangsu (CN); Yongzhen LI, Jiangsu (CN).

Signed and Sealed this
Twenty-seventh Day of August, 2024

Katherine Kelly Vidal
*Director of the United States Patent and Trademark Office*

SEQUENCE LISTING

<160> NUMBER OF SEQ ID NOS: 18

<210> SEQ ID NO 1
<211> LENGTH: 26
<212> TYPE: PRT
<213> ORGANISM: Artificial Sequence
<220> FEATURE:
<223> OTHER INFORMATION: HUMAN

<400> SEQUENCE: 1

Lys Ile Asn Thr Lys Ala Asn Asp Thr Ser Glu Glu Met Arg His Arg
1               5                   10                  15

Phe Arg Gln Leu Asp Thr Lys Leu Asn Asp
            20                  25

<210> SEQ ID NO 2
<211> LENGTH: 20
<212> TYPE: PRT
<213> ORGANISM: Artificial Sequence
<220> FEATURE:
<223> OTHER INFORMATION: HUMAN

<400> SEQUENCE: 2

Phe Lys Asn Glu Asp Asn Glu Thr Leu Ala Trp Glu Gly Val Met Lys
1               5                   10                  15

Glu Asn Tyr Leu
            20

<210> SEQ ID NO 3
<211> LENGTH: 20
<212> TYPE: PRT
<213> ORGANISM: Artificial Sequence
<220> FEATURE:
<223> OTHER INFORMATION: HUMAN

<400> SEQUENCE: 3

Asp Gly Thr Thr Tyr Asp Phe Ala His Cys Thr Phe Thr Gly Asn Glu
1               5                   10                  15

Ser Lys Pro Leu
            20

<210> SEQ ID NO 4
<211> LENGTH: 13
<212> TYPE: PRT
<213> ORGANISM: Artificial Sequence
<220> FEATURE:
<223> OTHER INFORMATION: HUMAN

<400> SEQUENCE: 4

Val Ser Arg Asn Leu Gly Pro Lys Ile Ile Met Leu Gln
1               5                   10

<210> SEQ ID NO 5
<211> LENGTH: 16
<212> TYPE: PRT
<213> ORGANISM: Artificial Sequence
<220> FEATURE:
<223> OTHER INFORMATION: HUMAN

<400> SEQUENCE: 5

Asp Glu Val Arg Gln Trp Tyr Val Asn Gly Val Asn Tyr Phe Thr Asp
1               5                   10                  15

<210> SEQ ID NO 6
<211> LENGTH: 17

```
<212> TYPE: PRT
<213> ORGANISM: Artificial Sequence
<220> FEATURE:
<223> OTHER INFORMATION: HUMAN

<400> SEQUENCE: 6

Leu Thr Val Ile Lys Met Glu Glu Ala Gly Asp Glu Ile Val Ser Asn
1               5                   10                  15

Ala

<210> SEQ ID NO 7
<211> LENGTH: 20
<212> TYPE: PRT
<213> ORGANISM: Artificial Sequence
<220> FEATURE:
<223> OTHER INFORMATION: HUMAN

<400> SEQUENCE: 7

Cys Lys Glu Lys Asn Met Glu Ser Ser Val Cys Cys Phe Lys Asn Glu
1               5                   10                  15

Asp Asn Glu Thr
            20

<210> SEQ ID NO 8
<211> LENGTH: 21
<212> TYPE: PRT
<213> ORGANISM: Artificial Sequence
<220> FEATURE:
<223> OTHER INFORMATION: HUMAN

<400> SEQUENCE: 8

Cys Ser Glu Glu Met Arg His Arg Phe Arg Gln Leu Asp Thr Lys Leu
1               5                   10                  15

Asn Asp Leu Lys Gly
            20

<210> SEQ ID NO 9
<211> LENGTH: 24
<212> TYPE: PRT
<213> ORGANISM: Artificial Sequence
<220> FEATURE:
<223> OTHER INFORMATION: HUMAN

<400> SEQUENCE: 9

Cys Phe Thr Gly Asn Glu Ser Lys Pro Leu Cys Val Glu Leu Asp Glu
1               5                   10                  15

His Asn Leu Pro Arg Phe Pro Glu
            20

<210> SEQ ID NO 10
<211> LENGTH: 16
<212> TYPE: PRT
<213> ORGANISM: Artificial Sequence
<220> FEATURE:
<223> OTHER INFORMATION: HUMAN

<400> SEQUENCE: 10

Asn Arg Arg Asn Asp Thr Leu Asp Ser Thr Arg Thr Leu Tyr Ser Ser
1               5                   10                  15

<210> SEQ ID NO 11
<211> LENGTH: 20
<212> TYPE: PRT
<213> ORGANISM: Artificial Sequence
<220> FEATURE:
```

<223> OTHER INFORMATION: HUMAN

<400> SEQUENCE: 11

Val Glu Val Glu Asp Ala Leu Thr Ser Ser Ala Val Lys Glu Lys Leu
1               5                   10                  15

Val Arg Phe Cys
            20

<210> SEQ ID NO 12
<211> LENGTH: 16
<212> TYPE: PRT
<213> ORGANISM: Artificial Sequence
<220> FEATURE:
<223> OTHER INFORMATION: HUMAN

<400> SEQUENCE: 12

Cys Glu Met Asp Ile Glu Leu His Asp Val Ser Pro Ile Thr Arg His
1               5                   10                  15

<210> SEQ ID NO 13
<211> LENGTH: 19
<212> TYPE: PRT
<213> ORGANISM: Artificial Sequence
<220> FEATURE:
<223> OTHER INFORMATION: HUMAN

<400> SEQUENCE: 13

Lys Glu Lys Asn Met Glu Ser Ser Val Cys Cys Phe Lys Asn Glu Asp
1               5                   10                  15

Asn Glu Thr

<210> SEQ ID NO 14
<211> LENGTH: 20
<212> TYPE: PRT
<213> ORGANISM: Artificial Sequence
<220> FEATURE:
<223> OTHER INFORMATION: HUMAN

<400> SEQUENCE: 14

Ser Glu Glu Met Arg His Arg Phe Arg Gln Leu Asp Thr Lys Leu Asn
1               5                   10                  15

Asp Leu Lys Gly
            20

<210> SEQ ID NO 15
<211> LENGTH: 23
<212> TYPE: PRT
<213> ORGANISM: Artificial Sequence
<220> FEATURE:
<223> OTHER INFORMATION: HUMAN

<400> SEQUENCE: 15

Phe Thr Gly Asn Glu Ser Lys Pro Leu Cys Val Glu Leu Asp Glu His
1               5                   10                  15

Asn Leu Pro Arg Phe Pro Glu
            20

<210> SEQ ID NO 16
<211> LENGTH: 26
<212> TYPE: PRT
<213> ORGANISM: Artificial Sequence
<220> FEATURE:
<223> OTHER INFORMATION: HUMAN

<400> SEQUENCE: 16

```
Asn Arg Arg Asn Asp Thr Leu Asp Ser Thr Arg Thr Leu Tyr Ser Ser
1               5                   10                  15

Ala Ser Arg Ser Thr Asp Leu Ser Tyr Ser
            20                  25

<210> SEQ ID NO 17
<211> LENGTH: 19
<212> TYPE: PRT
<213> ORGANISM: Artificial Sequence
<220> FEATURE:
<223> OTHER INFORMATION: HUMAN

<400> SEQUENCE: 17

Val Glu Val Glu Asp Ala Leu Thr Ser Ser Ala Val Lys Glu Lys Leu
1               5                   10                  15

Val Arg Phe

<210> SEQ ID NO 18
<211> LENGTH: 15
<212> TYPE: PRT
<213> ORGANISM: Artificial Sequence
<220> FEATURE:
<223> OTHER INFORMATION: HUMAN

<400> SEQUENCE: 18

Glu Met Asp Ile Glu Leu His Asp Val Ser Pro Ile Thr Arg His
1               5                   10                  15
```